United States Patent
Drew et al.

(10) Patent No.: US 7,926,487 B2
(45) Date of Patent: *Apr. 19, 2011

(54) RESPIRATORY MASK HAVING GAS WASHOUT VENT AND GAS WASHOUT VENT ASSEMBLY FOR A RESPIRATORY MASK

(75) Inventors: Joanne Elizabeth Drew, Balgowlah Heights (AU); Alexander Virr, Balmain (AU); Geoffrey Crumblin, Baulkham Hills (AU)

(73) Assignee: ResMed Limited, Bella Vista (AU)

( * ) Notice: Subject to any disclaimer, the term of this patent is extended or adjusted under 35 U.S.C. 154(b) by 1223 days.

This patent is subject to a terminal disclaimer.

(21) Appl. No.: 11/413,080

(22) Filed: Apr. 28, 2006

(65) Prior Publication Data

US 2006/0196509 A1  Sep. 7, 2006

Related U.S. Application Data

(63) Continuation of application No. 10/976,874, filed on Nov. 1, 2004, now Pat. No. 7,159,587, which is a continuation of application No. 10/377,110, filed on Mar. 3, 2003, now Pat. No. 6,823,865, which is a continuation of application No. 09/570,907, filed on May 15, 2000, now Pat. No. 6,581,594.

(51) Int. Cl.
*A62B 18/02* (2006.01)
(52) U.S. Cl. ......... 128/205.25; 128/206.21; 128/204.18; 128/207.12; 128/207.13
(58) Field of Classification Search .............. 128/205.25, 128/206.21, 204.18, 205.11, 207.12, 13, 128/200.29, 201.29

See application file for complete search history.

(56) References Cited

U.S. PATENT DOCUMENTS

| 781,516 A | 1/1905 | Guthrie |
| 812,706 A | 2/1906 | Warbasse |
| 835,075 A | 11/1906 | Mahaffy |
| 1,081,745 A | 12/1913 | Johnston et al. |

(Continued)

FOREIGN PATENT DOCUMENTS

AU  91/77110 B  11/1991

(Continued)

OTHER PUBLICATIONS

Japanese Office Action dated Feb. 17, 2009 3 pages and English Translation 3 pages.

(Continued)

*Primary Examiner* — Steven O Douglas
*Assistant Examiner* — Colin Stuart
(74) *Attorney, Agent, or Firm* — Nixon & Vanderhye P.C.

(57) ABSTRACT

The present invention provides a vent assembly suitable for use with a respiratory mask of the type used in CPAP treatment. In one embodiment the vent is made of a thin air permeable membrane. Generally, the membrane is thinner than 0.5 mm. The membrane can be made of a hydrophobic material such as polytetrafluoroethylene (PTFE). The membrane can also be fabricated from expanded PTFE. The expanded PTFE membrane is mounted on a polypropylene scrim. The pores of the membrane have a reference pore size of 10 to 15 microns. In an alternative embodiment, the vent assembly includes a vent constructed from stainless steel. In another embodiment the membrane has a superficial cross-sectional area of approximately 500 mm$^2$. In another embodiment the vent assembly comprises a membrane attached to a vent frame, the vent assembly forming an insert which can be removably attached to a mask frame.

92 Claims, 5 Drawing Sheets

U.S. PATENT DOCUMENTS

| | | |
|---|---|---|
| 1,192,186 A | 7/1916 | Greene |
| 1,653,572 A | 12/1927 | Jackson |
| 1,926,027 A | 9/1933 | Biggs |
| 2,008,677 A | 7/1935 | Booharin |
| 2,102,037 A | 12/1937 | Schwartz |
| 2,123,353 A | 7/1938 | Catt |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,843,121 A | 7/1958 | Hudson |
| 2,872,923 A | 2/1959 | Birch et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,162,411 A | 12/1964 | Duggan |
| 3,189,027 A | 6/1965 | Bartlett |
| 3,238,943 A | 3/1966 | Holley |
| 3,291,127 A | 12/1966 | Eimer et al. |
| 3,315,674 A | 4/1967 | Bloom at al. |
| 3,330,273 A | 7/1967 | Bennett |
| 3,362,420 A | 1/1968 | Blackburn et al. |
| 3,363,833 A | 1/1968 | Laerdal |
| 3,412,231 A | 11/1968 | McElligott |
| 3,490,452 A | 1/1970 | Greenfield |
| 3,556,122 A | 1/1971 | Laerdal |
| 3,580,051 A | 5/1971 | Blevins |
| 3,680,556 A | 8/1972 | Morgan |
| 3,700,000 A | 10/1972 | Hesse et al. |
| 3,720,235 A | 3/1973 | Schrock |
| 3,796,216 A | 3/1974 | Schwarz |
| 3,799,164 A | 3/1974 | Rollins |
| D231,803 S | 6/1974 | Huddy |
| 3,850,171 A | 11/1974 | Ball et al. |
| 3,868,164 A | 2/1975 | Lisk |
| 3,877,425 A | 4/1975 | O'Neill |
| 3,942,403 A | 3/1976 | Pramberger |
| 3,949,743 A | 4/1976 | Shanbrom |
| 3,958,275 A | 5/1976 | Morgan et al. |
| 4,037,142 A | 7/1977 | Poole |
| 4,077,404 A | 3/1978 | Elam |
| D250,131 S | 10/1978 | Lewis et al. |
| 4,167,185 A | 9/1979 | Lewis |
| 4,201,205 A * | 5/1980 | Bartholomew .......... 128/205.25 |
| 4,219,020 A | 8/1980 | Czajka |
| 4,226,234 A | 10/1980 | Gunderson |
| 4,245,632 A | 1/1981 | Houston |
| 4,258,710 A | 3/1981 | Reber |
| 4,266,540 A | 5/1981 | Panzik et al. |
| 4,274,406 A | 6/1981 | Bartholomew |
| 4,276,877 A | 7/1981 | Gdulla |
| D262,322 S | 12/1981 | Mizerak |
| 4,304,229 A | 12/1981 | Curtin |
| 4,328,797 A | 5/1982 | Rollins, III et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,440,163 A | 4/1984 | Spergel |
| 4,454,881 A | 6/1984 | Huber et al. |
| 4,467,799 A | 8/1984 | Steinberg |
| 4,522,639 A | 6/1985 | Ansite et al. |
| 4,558,710 A | 12/1985 | Eichler |
| 4,559,939 A | 12/1985 | Levine et al. |
| 4,580,556 A | 4/1986 | Kondur |
| 4,616,647 A | 10/1986 | McCreadie |
| 4,622,964 A | 11/1986 | Flynn |
| 4,648,394 A | 3/1987 | Wise |
| 4,649,912 A | 3/1987 | Collins |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,969,901 A | 11/1990 | Binder |
| 4,971,051 A | 11/1990 | Toffolon |
| 4,974,586 A | 12/1990 | Wandel et al. |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,018,519 A | 5/1991 | Brown |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,512 A | 9/1991 | Murchie |
| 5,063,922 A | 11/1991 | Hakkinen |
| 5,065,756 A | 11/1991 | Rapoport |
| 5,069,205 A | 12/1991 | Urso |
| 5,080,094 A | 1/1992 | Tayebi |
| D323,908 S | 2/1992 | Hollister et al. |
| 5,109,839 A | 5/1992 | Blasdell et al. |
| 5,109,840 A | 5/1992 | Daleiden |
| 5,117,819 A | 6/1992 | Servidio et al. |
| 5,121,745 A | 6/1992 | Israel |
| 5,133,347 A | 7/1992 | Huennebeck |
| 5,140,982 A | 8/1992 | Bauman |
| 5,148,802 A | 9/1992 | Sanders et al. |
| 5,159,938 A | 11/1992 | Laughlin |
| 5,178,138 A | 1/1993 | Walstrom et al. |
| D334,633 S | 4/1993 | Rudolph |
| 5,231,983 A | 8/1993 | Matson et al. |
| 5,233,978 A | 8/1993 | Callaway |
| 5,243,971 A | 9/1993 | Sullivan |
| 5,245,995 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,297,544 A | 3/1994 | May |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,368,020 A | 11/1994 | Beux |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebl |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |

| | | | | | | |
|---|---|---|---|---|---|---|
| 5,538,000 | A | 7/1996 | Rudolph | DE | 197 35 359 | | 1/1998 |
| 5,540,223 | A | 7/1996 | Starr et al. | DE | 297 23 101 | | 7/1998 |
| 5,542,128 | A | 8/1996 | Lomas | DE | 298 10846 | U1 | 8/1998 |
| RE35,339 | E | 10/1996 | Rapoport | EP | 0 054 154 | | 10/1981 |
| 5,560,354 | A | 10/1996 | Berthon-Jones et al. | EP | 0 252 052 | A1 | 1/1988 |
| 5,570,682 | A | 11/1996 | Johnson | EP | 0 264 772 | A1 | 4/1988 |
| 5,570,689 | A | 11/1996 | Starr et al. | EP | 0 386 605 | A1 | 2/1990 |
| 5,575,277 | A | 11/1996 | Lutz et al. | EP | 0427474 | A2 | 5/1991 |
| D377,089 | S | 12/1996 | Starr et al. | EP | 0 462 701 | A1 | 12/1991 |
| 5,592,938 | A | 1/1997 | Scarberry et al. | EP | 0 602 424 | | 11/1993 |
| 5,608,647 | A | 3/1997 | Rubsamen et al. | EP | 0601708 | | 6/1994 |
| 5,642,730 | A | 7/1997 | Baran | EP | 0 608 684 | A1 | 8/1994 |
| 5,645,049 | A | 7/1997 | Foley et al. | EP | 0 697 225 | | 7/1995 |
| 5,647,355 | A | 7/1997 | Starr et al. | EP | 0697 225 | A2 | 7/1995 |
| 5,647,357 | A | 7/1997 | Barnett et al. | EP | 0 697 225 | A2 | 2/1996 |
| 5,649,532 | A | 7/1997 | Griffiths | EP | 178 925 | A2 | 4/1996 |
| 5,649,533 | A | 7/1997 | Oren | EP | 0 747 078 | A2 | 12/1996 |
| 5,655,520 | A | 8/1997 | Howe et al. | EP | 0 821 978 | | 2/1998 |
| 5,655,527 | A | 8/1997 | Scarberry et al. | EP | 1 027 905 | A | 8/2000 |
| 5,657,493 | A | 8/1997 | Ferrero et al. | EP | 1 163 923 | A2 | 6/2001 |
| 5,657,752 | A | 8/1997 | Landis et al. | FR | 2 574 657 | A1 | 6/1986 |
| 5,662,101 | A | 9/1997 | Ogden et al. | FR | 2 658 725 | A1 | 8/1991 |
| 5,666,946 | A | 9/1997 | Langenback | FR | 2 749 176 | | 12/1997 |
| 5,685,296 | A | 11/1997 | Zdrojkowski et al. | GB | 799 225 | | 8/1958 |
| 5,687,715 | A | 11/1997 | Landis et al. | GB | 1395391 | | 5/1975 |
| 5,709,204 | A * | 1/1998 | Lester ............... 128/205.25 | GB | 1 467 828 | | 3/1977 |
| 5,715,741 | A | 2/1998 | Gasser et al. | GB | 2145335 | A | 3/1985 |
| 5,715,814 | A | 2/1998 | Ebers | GB | 2147506 | A | 5/1985 |
| 5,732,695 | A | 3/1998 | Metzger | GB | 2 164 569 | A | 3/1986 |
| 5,746,201 | A | 5/1998 | Kidd | GB | 2 236 681 | A | 4/1991 |
| 5,765,553 | A | 6/1998 | Richards et al. | GB | 2 267 648 | A | 12/1993 |
| 5,813,423 | A | 9/1998 | Kirchgeorg | JP | 63105772 | | 5/1988 |
| 5,832,918 | A | 11/1998 | Pantino | JP | 2-141775 | | 11/1990 |
| 5,836,303 | A * | 11/1998 | Hurst et al. ............ 128/206.24 | JP | 7000521 | | 1/1995 |
| 5,839,433 | A | 11/1998 | Higenbottam | JP | 9010311 | | 1/1997 |
| 5,878,742 | A | 3/1999 | Figueredo et al. | JP | 09/216240 | A | 8/1997 |
| 5,921,239 | A | 7/1999 | McCall et al. | JP | A-11-267234 | | 10/1999 |
| 5,937,851 | A | 8/1999 | Serowski et al. | JP | A-2000-140587 | | 5/2000 |
| 6,006,748 | A | 12/1999 | Hollis | JP | 2000-279520 | | 10/2000 |
| 6,019,101 | A | 2/2000 | Cotner et al. | JP | 2001-511035 | | 8/2001 |
| 6,039,044 | A | 3/2000 | Sullivan | JP | 2002-95751 | | 4/2002 |
| 6,112,746 | A | 9/2000 | Kwok et al. | JP | 2004-535226 | | 11/2004 |
| 6,119,693 | A | 9/2000 | Kwok et al. | WO | WO 80/01044 | | 5/1980 |
| 6,135,109 | A | 10/2000 | Blasdell et al. | WO | WO 82/03548 | | 10/1982 |
| 6,192,886 | B1 | 2/2001 | Rudolph | WO | WO 86/06969 | | 12/1986 |
| 6,309,438 | B1 | 10/2001 | Kanno et al. | WO | WO 87/01950 | | 4/1987 |
| 6,435,181 | B1 * | 8/2002 | Jones et al. ............ 128/204.18 | WO | WO 91/03277 | | 3/1991 |
| 6,491,034 | B1 * | 12/2002 | Gunaratnam et al. ... 128/204.18 | WO | WO 92/15353 | | 9/1992 |
| 6,561,190 | B1 | 5/2003 | Kwok | WO | WO 92/20395 | | 11/1992 |
| 6,561,191 | B1 | 5/2003 | Kwok | WO | WO 93/01854 | | 2/1993 |
| 6,581,594 | B1 | 6/2003 | Drew et al. | WO | WO 94/02190 | | 2/1994 |
| 6,584,976 | B2 | 7/2003 | Japuntich et al. | WO | WO 94/16759 | | 8/1994 |
| 6,644,316 | B2 * | 11/2003 | Bowman et al. ......... 128/207.12 | WO | WO 94/20501 | | 9/1994 |
| 6,668,830 | B1 | 12/2003 | Hansen et al. | WO | WO 95/02428 | | 1/1995 |
| 6,823,865 | B2 | 11/2004 | Drew et al. | WO | WO 96/17643 | | 6/1996 |
| 7,159,587 | B2 | 1/2007 | Drew et al. | WO | WO 96/25983 | | 8/1996 |
| 7,207,335 | B2 | 4/2007 | Kwok | WO | WO 96/39206 | | 12/1996 |
| 2003/0079751 | A1 | 5/2003 | Kwok | WO | WO 97/07847 | | 3/1997 |
| 2003/0116160 | A1 | 6/2003 | Kwok et al. | WO | WO 97/41911 | | 11/1997 |
| 2005/0092326 | A1 | 5/2005 | Drew et al. | WO | WO 97/46281 | * | 12/1997 |
| | | | | WO | WO 98/04310 | | 2/1998 |
| | | FOREIGN PATENT DOCUMENTS | | WO | WO 98/11930 | | 3/1998 |
| AU | | 94/64816 B | 12/1994 | WO | WO 98/18514 | | 5/1998 |
| AU | | 95/16178 B | 7/1995 | WO | WO 98/24499 | | 6/1998 |
| AU | | 9459430 | 2/1996 | WO | WO 98/26829 | | 6/1998 |
| AU | | A 32914/95 | 2/1996 | WO | WO 98/26830 | | 6/1998 |
| AU | | A 41018/97 | 4/1998 | WO | WO 98/34665 | | 8/1998 |
| AU | | A 89312/98 | 1/1999 | WO | WO 98/48878 | | 11/1998 |
| AU | | 712236 | 4/1999 | WO | WO 02/096342 | | 12/2002 |
| CA | | 1039144 | 9/1978 | | | | |
| DE | | 459104 | 4/1928 | | | | |
| DE | | 701690 | 1/1941 | | | | |
| DE | | 159396 | 6/1981 | | | | |
| DE | | 3015279 A1 | 10/1981 | | | | |
| DE | | 3345067 A1 | 6/1984 | | | | |
| DE | | 3537507 A1 | 4/1987 | | | | |
| DE | | 3539073 A1 | 5/1987 | | | | |
| DE | | 4004157 C1 | 4/1991 | | | | |
| DE | | 4343206 A1 | 6/1995 | | | | |

OTHER PUBLICATIONS

Translation of Official Action for Japanese Patent Application No. 2001-381410 issued Jun. 6, 2007 (2 pages).
U.S. Appl. No. 10/298,845, Kwok, filed Nov. 19, 2002.
U.S. Appl. No. 11/645,582, Kwok, filed Dec. 27, 2006.
Notice of Allowance issued in Japanese Patent Appln. No. 2007-028683 (Sep. 7, 2010), which cites prior art in the Notice of Allowance.

Notice of Reasons for Rejection issued in Japanese Appln. No. 2007-305204 (May 25, 2010) w/English translation.
Office Action issued in Japanese Appln. No. 2007-028683, mailed Nov. 17, 2009 (W/English translation).
Mask 1 Photographs, Respironics Inc., Reusable Full Mask (small) Part # 452033 Lot #951108.
Mask 2 Photographs, Puritan—Bennett, Adam Curcult , Shell Part # 231700, Swivel Part # 616329.00, Pillows (medium) Part #616324.
Mask 3, Photographs, DeVilbiss Healthcare Inc., DeVilbiss Seal-Ring and CPAP Mask Kit (medium), Part 73510-689.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510-668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.
Search Report issued in related European Patent Appln. No. 10 18 1365.7 (Dec. 3, 2010).
Search Report issued in related European Patent Appln. No. 10 18 1509.0 (Dec. 3, 2010).

* cited by examiner

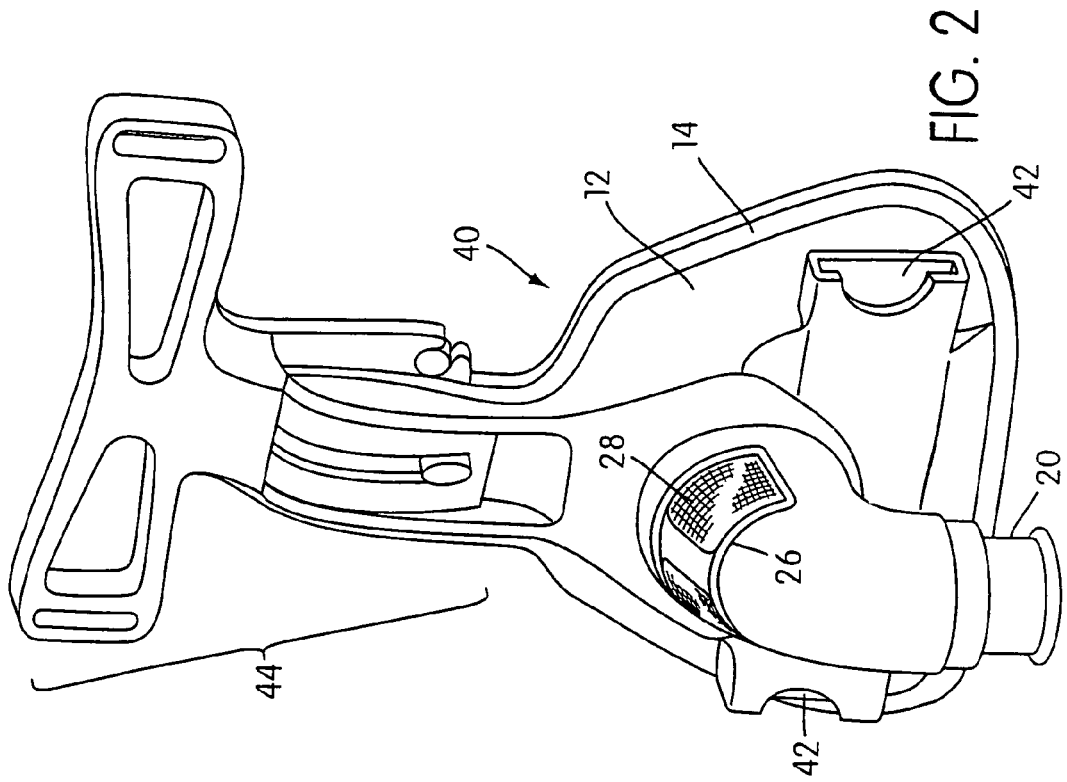
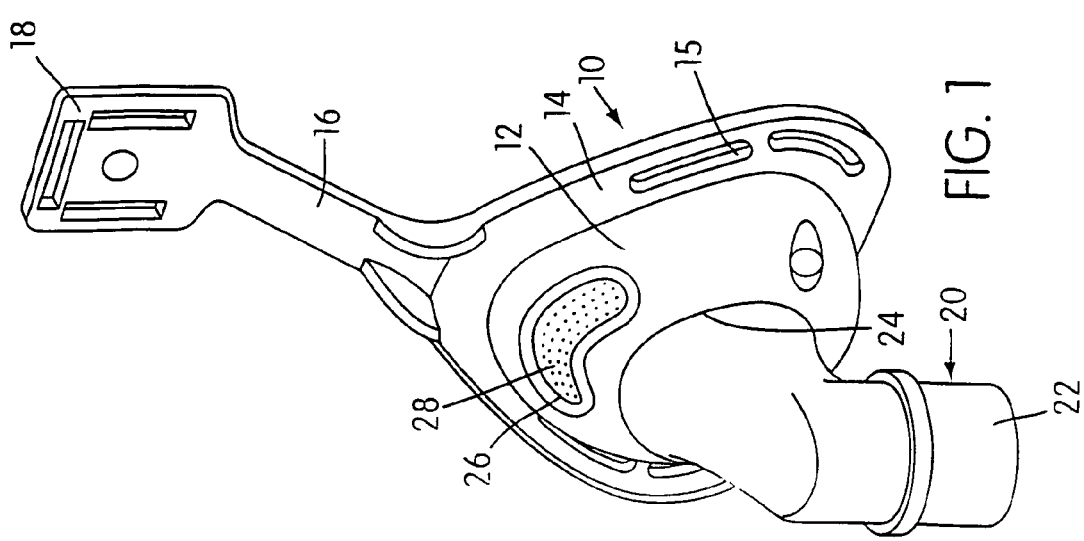

RESPIRATORY MASK HAVING GAS WASHOUT VENT AND GAS WASHOUT VENT ASSEMBLY FOR A RESPIRATORY MASK

CROSS REFERENCE TO RELATED APPLICATIONS

This application is a continuation of U.S. application Ser. No. 10/976,874, filed Nov. 1, 2004, now allowed, which is a continuation of U.S. application Ser. No. 10/377,110, filed Mar. 3, 2003, now U.S. Pat. No. 6,823,865, which is a continuation of U.S. application Ser. No. 09/570,907, filed May 15, 2000, now U.S. Pat. No. 6,581,594, each incorporated herein by reference in its entirety.

BACKGROUND OF INVENTION

1. Field of the Invention

The present invention relates to a respiratory mask and a vent for a respiratory mask.

2. General Background and Related Art

The application of Continuous Positive Airway Pressure (CPAP) via a nasal mask is a common ameliorative treatment for sleep disordered breathing (SDB) including obstructive sleep apnea (OSA) as described in commonly-assigned U.S. Pat. No. 4,944,310. In CPAP treatment for OSA, air or other breathable gas is supplied to the entrance of a patient's airways at a pressure elevated above atmospheric pressure, typically in the range 3-20 cm $H_2O$ as measured in the patient interface. It is also known for the level of treatment pressure to vary during a period of treatment in accordance with patient need, that form of CPAP being known as automatically adjusting nasal CPAP treatment, as described in commonly-assigned U.S. Pat. No. 5,245,995.

Non-invasive positive pressure ventilation (NIPPV) is another form of treatment for breathing disorders including sleep disordered breathing. In a basic form, NIPPV involves a relatively high pressure of gas being provided in the patient interface during the inspiratory phase of respiration and a relatively low pressure or atmospheric pressure being provided in the patient interface during the expiratory phase of respiration. In other NIPPV modes the pressure can be made to vary in a complex manner throughout the respiratory cycle. For example, the pressure at the patient interface during inspiration or expiration can be varied through the period of treatment as disclosed in commonly-assigned International PCT Patent Application No. WO 98/12965 and International PCT Patent Application No WO 99/61088.

In this specification any reference to CPAP treatment is to be understood as embracing all of the above-described forms of ventilatory treatment or assistance.

Typically, the patient interface for CPAP treatment consists of a nasal mask. The nasal mask is generally defined by a mask shell which forms an inner cavity defined by its interior surface, mask cushion and the user's face, a gas inlet which may or may not include a separate component such as a swivel elbow. Alternatively, a nose-mouth mask or full-face mask or nasal prongs or nasal pillows can be used. In this specification any reference to a mask is to be understood as incorporating a reference to a nasal mask, nose-mouth mask, full face mask, nasal prongs or nasal pillows unless otherwise specifically indicated. The mask incorporates, or has in close proximity, a gas washout vent for venting exhaled gases to atmosphere. The gas washout vent (the vent) is sometimes referred to as a $CO_2$ washout vent.

It is important that the apparatus is quiet and comfortable to encourage patient compliance with therapy. The exhausting to atmosphere of exhaled gas through the vent creates noise. As CPAP and NIPPV treatments are normally administered while the patient is sleeping, minimization of such noise is desirable for both the comfort of the patient and any bed partner.

From a clinical perspective it is desirable for a mask and vent combination to maximize both the elimination of exhaled $CO_2$ through the vent and also the inhalation of the supplied breathable gas. In this way, retention of exhaled $CO_2$ within the mask, which is "re-breathed" by the wearer, is minimized. Generally by locating the vent in the mask shell $CO_2$ washout will be superior to locating the same vent between the mask shell and the breathable gas supply conduit.

It is desirable to minimize the weight of the vent assembly for greater patient comfort.

Systems for the delivery of nasal CPAP treatment often incorporate in-line humidifiers to minimize drying of the nasal mucosa and increase patient comfort. Accordingly, it is also desirable that a vent not block when used with humidified gas. It is also desirable that a vent be easily cleaned or economically disposable.

A number of vent configurations are known. One approach to vent configuration is to create within the mask shell one or more openings that allow for the flow of exhaust gas from the inner cavity to atmosphere. The exhaust flow may be directed through the incorporation of an additional pipe extending out from the opening located on the mask shell outer surface.

The assignee's nasal mask system known by the name ResMed Modular Mask System incorporates an outlet vent located in the swivel elbow connected to the mask shell. The ports defining the vent have the same cross-sectional thickness and are formed from the same polycarbonate material that is used to form the swivel elbow and mask shell frame.

The whisper swivel, manufactured by Respironics, Inc provides three slots on the circumference of a generally cylindrical attachment piece. In use, the attachment piece is to be interposed between the mask shell and the gas conduit. The attachment piece is made of the same material and thickness as is used to make the mask shell.

European Patent No. 0 697 225 discloses a vent formed from a porous sintered material.

A known vent, manufactured by Gottleib Weinmann Gerate Fur Medizin Und Arbeitsschutz GmbH and Co. comprises a generally cylindrical insert to be interposed in use, between the mask shell and the gas conduit. The insert includes a window which is covered with a porous sintered material of approximately 3-4 mm thickness.

Another type of vent intended to be inserted between the mask shell and the breathable gas supply conduit is the E-Vent N by Draeger medizintechnik GmbH (the Draeger vent). The Draeger vent comprises a stack of 21 annular disks, which have slots in their adjacent surfaces for gas to flow therethough. Each slot has a length of 5 to 7 mm as measured along the path from the interior of the vent to atmosphere.

The assignee produces a respiratory mask known as the MIRAGE® nasal mask system and the MIRAGE® full-face mask (the MIRAGE® mask). The MIRAGE® mask has a crescent shaped opening in the mask shell in which is located a complementary shaped crescent elastomeric insert with six holes therein which constitutes the vent. The elastomeric inset has a cross-sectional thickness of 3 to 4 mm. The vent of the type used in the MIRAGE® is described in International Patent Application No. WO 98/34665 and Australian Patent No 712236.

It is an object of the present invention to provide an alternative form of vent that is suitable for use in a respiratory mask.

SUMMARY OF THE INVENTION

The present invention provides a vent assembly suitable for use with a mask used in CPAP treatment wherein the vent assembly is a thin air permeable membrane.

In one form of the invention, the membrane is thinner than the mask frame.

In another form of the invention, the membrane is thinner than 0.5 mm.

In another form of the invention the membrane has an approximate thickness of 0.05 mm.

In another form of the invention the membrane is constructed from a hydrophobic material such as polytetrafluoroethylene (PTFE).

In another form of the invention the membrane is constructed from expanded PTFE.

In another form of the invention the expanded PTFE membrane is mounted on a polypropylene scrim.

In another form, the pores of the membrane have a reference pore size of 10 to 15 microns.

In another form of the invention the membrane is constructed from stainless steel.

In another form of the invention the membrane of the vent has a superficial cross-sectional area of approximately 500 mm$^2$.

In another form of the invention the vent assembly comprises a membrane attached to a vent frame, the vent assembly forming an insert which can be removeably attached to a mask fame.

In another form of the invention there is provided a respiratory mask for communicating breathable gas to the entrance of a wearer's airways, the mask including (i) mask shell, (ii) a gas inlet and (iii) an opening into which an insert constructed from a thin air permeable membrane with a corresponding shape may be placed. The opening may be positioned in the mask shell or in the gas inlet.

In one form, the mask includes a mask shell with an integrally formed gas inlet and the opening is provided in the mask shell remote the inlet. In another form, the mask includes a mask shell with an integrally formed gas inlet and the opening is provided in the gas inlet. In yet another form, the mask includes a mask shell with a separately formed gas inlet attached thereto and the opening is provided in the mask shell remote the inlet. In still yet another form, the mask includes a mask shell with a separately formed gas inlet attached thereto and the opening is provided in the gas inlet.

The present invention also provides a respiratory mask arrangement for communicating breathable gas to the entrance of a wearer's airways, the mask arrangement including a vent assembly comprising an opening with a thin air permeable membrane extending across an opening.

The present invention also provides an apparatus for delivering CPAP which apparatus includes a mask arrangement for communicating breathable gas to the entrance of a wearer's airways, the mask arrangement including a gas washout vent assembly comprising an opening with a thin air permeable membrane extending across said opening.

BRIEF DESCRIPTION OF THE DRAWINGS

FIG. 1 is a perspective view of a respiratory mask according to a first embodiment of the invention;

FIG. 2 is a perspective view of a respiratory mask according to a second embodiment of the invention;

DETAILED DESCRIPTION

Figure 3:
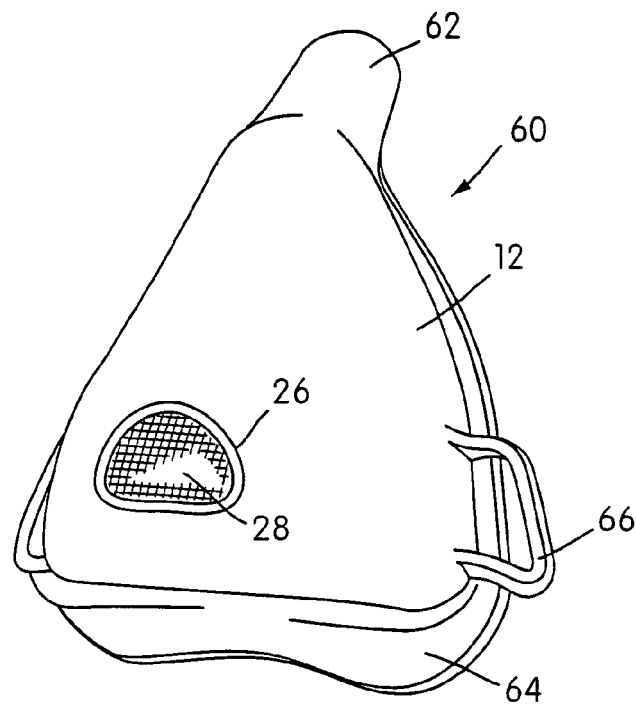
FIG. 3 is a perspective view of a respiratory mask according to a third embodiment of the invention.

FIG. 1 shows a nasal respiratory mask 10 according to a first embodiment of the invention. The mask 10 includes a rigid plastic mask shell 12, which has a peripheral flange 14 for mounting of a cushion (not shown) to the shell 12. The cushion abuts the wearer's face in use and is well known in the art. The flange 14 includes slots 15 for the connection of mask restraining straps (not shown) that extend around the head of the wearer to maintain the mask 10 adjacent to the wearer's face. The straps are also known in the art. The shell 12 also includes an arm 16, which terminates in a fitting 18 that is adapted to connect to a forehead support (not shown), which is also known in the art.

The mask shell 12 includes a breathable gas inlet 20 which is rotatably mounted to the shell 12. The inlet 20 has a first end 22 which is adapted for connection with a breathable gas supply conduit (not shown) and a second end 24 which is adapted to connect to, and communicate the supplied gas to the interior of the shell 12 for subsequent communication with the wearer's airways.

The mask 10 includes a gas washout vent constituted by an opening 26 in the shell 12 across which extends a thin air permeable membrane 28.

In the FIG. 1 embodiment, the thin air permeable membrane 28 is a stainless steel sheet approximately 0.45 mm thick having holes with a diameter approximately 0.1 mm in diameter. The total open area is approximately 5% of the total superficial surface area of the sheet. The dimensions of the sheet are approximately 322 mm$^2$. The holes are laser cut into the stainless steel. The holes are desirably laser cut or flame cut through the stainless steel.

Preferably the holes have a diameter of less than 0.2 mm, and preferably provide a total open area of approximately 1% to 25% of the superficial surface area of the steel. The holes may be tapered (in a gradual or stepped manner) through their internal bore. In use, if the smaller end of the vent's openings are located on the atmosphere side the opportunity for blockage occurring by the insertion of particulate matter will be minimized. Alternatively, the larger end of the vent's openings may be located on the atmosphere side which may make the vent quieter.

FIG. 2 shows a nasal respiratory mask 40 according to a second embodiment of the invention. Like reference numerals to those used in describing the first embodiment will be used to denote like features in respect of the second embodiment. Accordingly, the mask 40 has a shell 12 with a gas inlet 20. Instead of the slots 15 of the first embodiment the mask shell includes openings 42 which are adapted to snap engage with connection fittings (not shown) provided on the end of mask restraining straps (not shown). Further, instead of the arm 16 and fitting 18, the mask 40 includes an adjustable forehead support mechanism indicated generally by the reference numeral 44.

The mask 40 also includes a vent constituted by an opening 26 formed in the gas inlet 20 across which extends a thin air permeable membrane 28.

FIG. 3 shows a mask 60 according to a third embodiment of the present invention. Although this particular embodiment is directed to a nasal mask, it should be noted that various vent arrangements can be used with various mask arrangements. Once again like reference numerals to those used in describing features of the first embodiment shall be used to denote like features in respect of the third embodiment. The mask 60 includes a mask shell 12 with an integrally formed fixed gas inlet 62. A cushion 64 is attached to the peripheral flange 14 of the shell 12. The shell 12 also includes slotted extensions 66 for connecting headgear (not shown) to the mask. The mask 60 includes an opening 26 across which is extended a thin air permeable membrane 28 of identical construction to the ePTFE membrane discussed below in relation to the mask 40 shown in FIG. 6.

Figure 4:
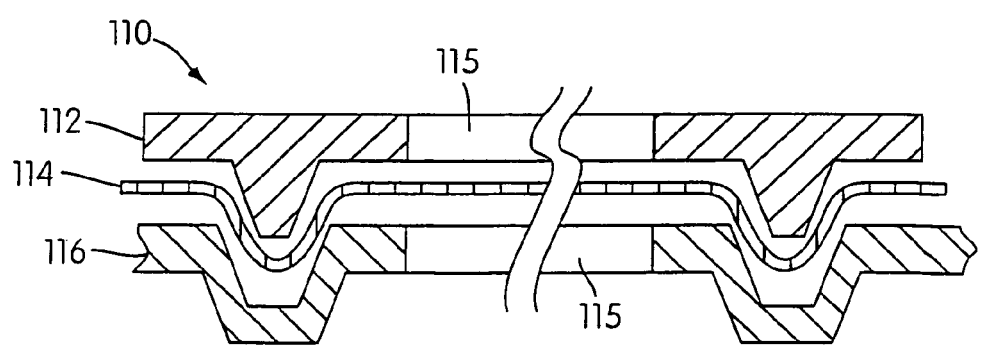
FIG. 4 is a partial cross-sectional view of a vent assembly according to a fourth embodiment of the invention.

FIG. 4 shows a cross-section of vent assembly 110. There is provided a membrane 114 interposed between an outer element 112 and an inner element 116. This arrangement provides for a simple assembly. There is a corresponding opening 115 in the outer element 112 and inner element 116 to allow for the passage of air through the membrane. The inner element 116 may form part of the mask frame or of a separate insert to be positioned in an opening in the mask frame.

Figure 5:
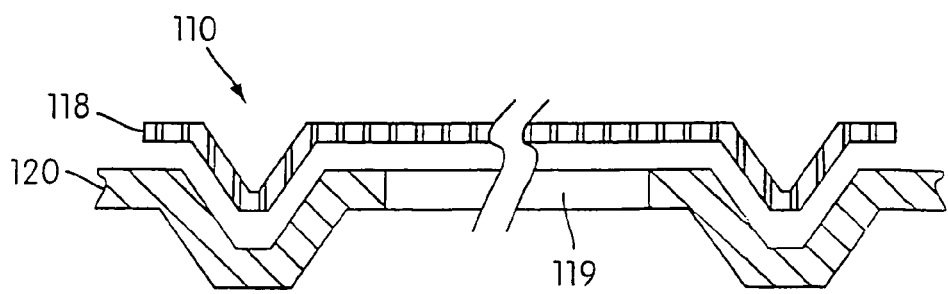
FIG. 5 is a partial cross-sectional view of a vent assembly according to a fifth embodiment the invention.

FIG. 5 shows an alternative cross-section of a vent assembly 110. There is provided a stainless steel membrane insert 118 positioned over the inner element 120. There is an opening 119 in the inner element 120 to allow for the passage of air through the membrane. The inner element 119 may form part of the mask frame or of a separate insert to be positioned in an opening in the mask frame.

Figure 7:
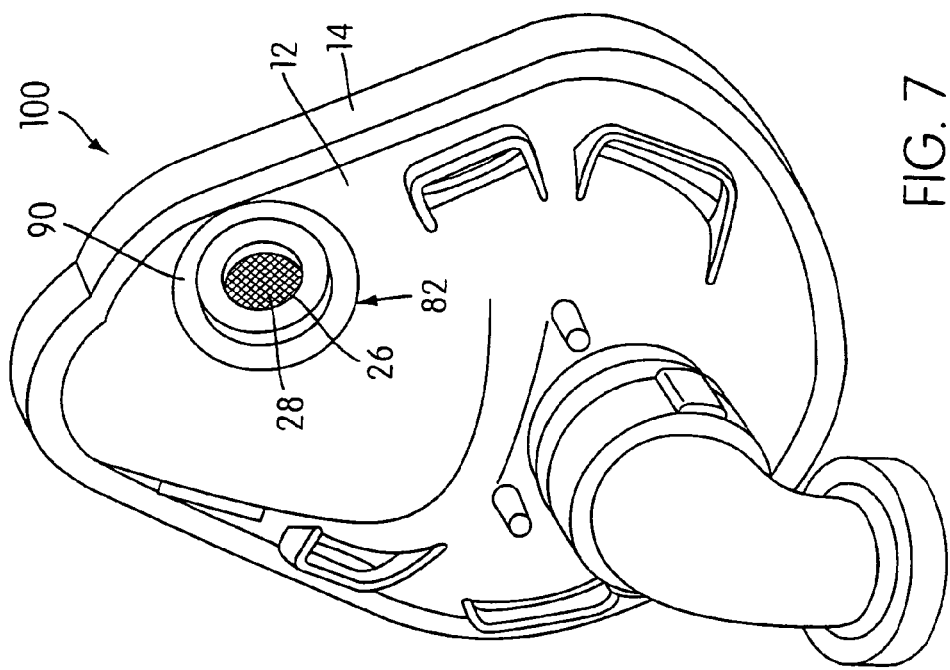
FIG. 7 is a perspective view of a full-face mask according to a seventh embodiment of the invention.
Figure 6:
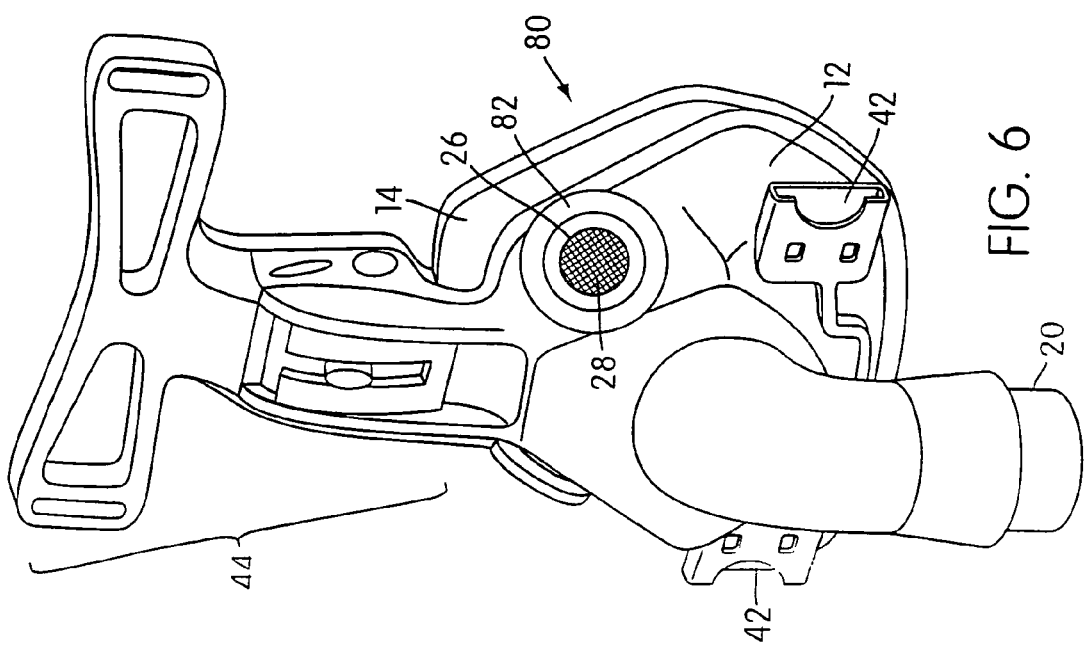
FIG. 6 is a perspective view of a respiratory mask according to sixth embodiment of the invention.

FIG. 6 shows a nasal respiratory mask 80 according to a sixth embodiment of the invention. The mask 80 is similar to the second embodiment of the mask 40 shown in FIG. 2 and like reference numerals have been used to indicate like features with respect to the second embodiment. In the mask 40 of FIG. 2, the vent is provided in the gas inlet 20, whereas in the mask 80 the vent is provided in the shell 12. More particularly, the mask 80 includes two cylindrical inserts 82 which have an inner opening 26 across which extends the thin air permeable material 28. The thin air permeable material is made from GORE-TEX® product attached to a polypropylene scrim having an area of 481 mm². The membrane is constructed from expanded polytetrafluoroethylene (ePTFE). The inventors have identified GORE-TEX® ePTFE product manufactured by W. L. Gore & Associates, Inc. of Maryland USA (GORE-TEX® membrane) as being a suitable material for constructing a membrane. In one preferred form, the GORE-TEX® membrane has the following characteristics:
Membrane material 100% expanded polytetrafluoroethylene
Reference pore size 10-15 micron
Bubble Point typical minimum individual 0.02 bar
Airflow 0.37 LPM/cm²
Thickness 0.05 mm
Substrate polypropylene scrim FIG. 7 shows a seventh embodiment of a full-face respiratory mask 100 according to the invention. Once again like reference numerals to those used in denoting like features with previous embodiments have been used to denote like features in respect of this embodiment. The mask 100 is similar to the mask 80 shown in FIG. 6 in that the vent is provided in the inserts 82. However the mask 100 uses slotted extensions 66 to attach mask restraining straps (not shown), not openings 42.

Figure 8:
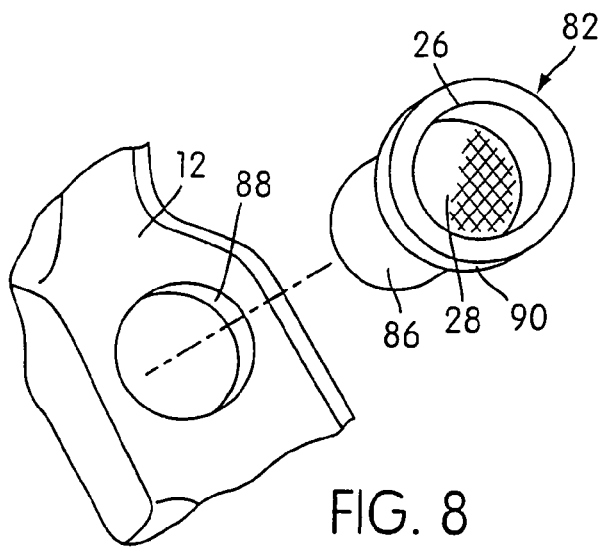
FIG. 8 is an enlarged detailed view of an insert suitable for use with the masks shown in FIG. 6 and FIG. 7.

As best seen in FIG. 8, which is a close-up view of the insert shown in FIG. 6, the insert 82 is comprises a cylindrical portion 86 sized to be a snug fit into a circular orifice 88 provided in the mask shell 12. The insert 82 located against the outer surface of the shell 12 by a peripheral flange 90. The inserts may be glued in position.

Figure 9:
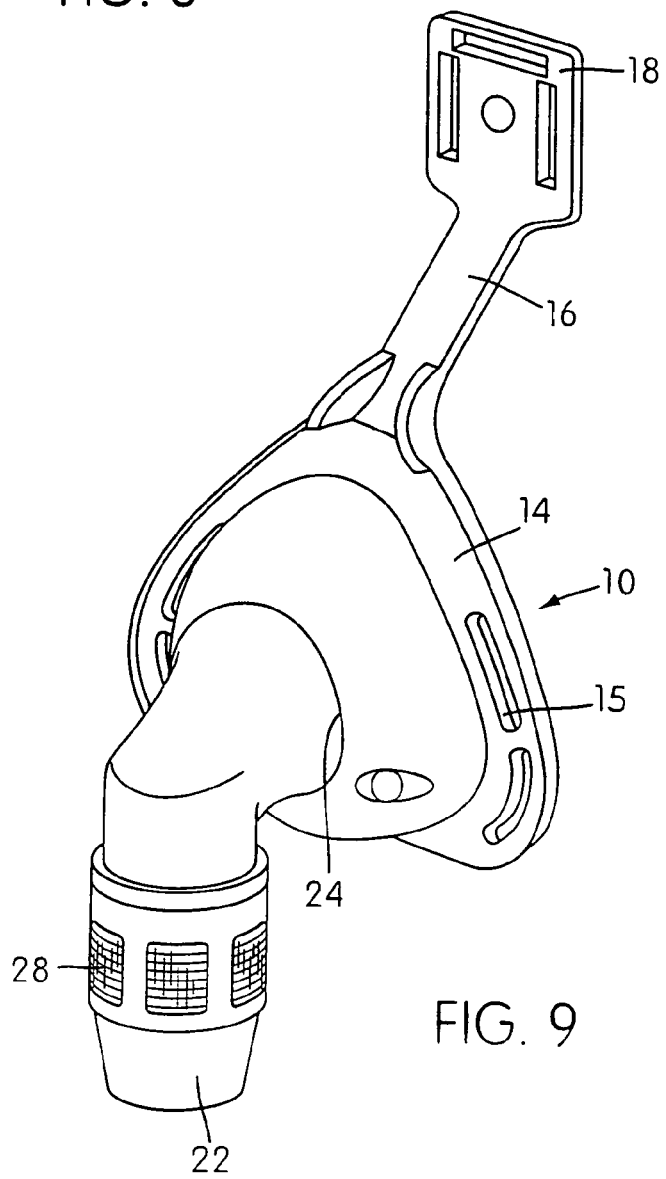
FIG. 9 is a perspective view of a vent assembly according to an eighth embodiment of the invention where the thin air permeable membrane is located in a cylindrical position on a tube suitable for attachment to the mask elbow.

FIG. 9 shows a further embodiment of the invention in which an in-line vent assembly is provided. Like numerals are used to indicate like features with previous embodiments. In this embodiment, the in-line vent assembly comprises a generally cylindrical shaped vent frame with "windows" or "ports" covered with a membrane as described above.

The thin air permeable membrane of the present invention may be attached to the mask by any suitable means. For examples the stainless steel vent described above may be attached to a polycarbonate mask shell by way of hot glue adhesive (for example) or any other suitable adhesive. The durability sought to be achieved will determine the suitable approach for attachment.

In a further embodiment there is provided a means to indicate the volume of air that has passed through the vent, or alternatively the time that the vent assembly has been used. When a sufficient volume of air has passed through the vent assembly, or the assembly has been used for a sufficient time and may have become blocked, the indicator will signal that the vent assembly should be replaced.

For convenience, the thin air permeable membrane can be provided in an insert which is releasably attachable to the mask shell via a push-fit mechanism, as shown in FIG. 8. Preferably on at least the outer surface of the insert there is provided at least one cross-piece that protects the air permeable membrane from being damaged as it is located into the receiving orifice of the mask shell. This approach will allow for the easy placement, removal and replacement of a vent insert while retaining the other components of the mask. While the insert may be configured to take the form of any requisite shape preferably the insert has a circular circumferential shape defining a cylindrical insert which has a frictional fit within a corresponding circular orifice in the mask shell or gas inlet.

Formation of the vent through use of an insert configuration facilitates the selection and fitting of a vent to suit a user's requirements. For example where a low treatment pressure is required the associated flow will also be relatively small compared with flow required to achieve a higher treatment pressure. In such circumstances a relatively large vent area may be adopted to facilitate achievement of the clinically desirable mask $CO_2$ washout rate. Should a higher treatment pressure be required then the previously selected vent may be exchanged for a vent being more restrictive to flow. The more restrictive vent will allow achievement of the clinically desirable mask $CO_2$ washout rate while avoiding the intensity of noise and exhaust gas jetting that would occur had the previously selected low pressure vent been used with the higher treatment pressure.

Locating the vent in the mask shell results in an improvement in the minimization of $CO_2$ retention within the mask compared to locating the vent as an inline mask component.

Figure 10:
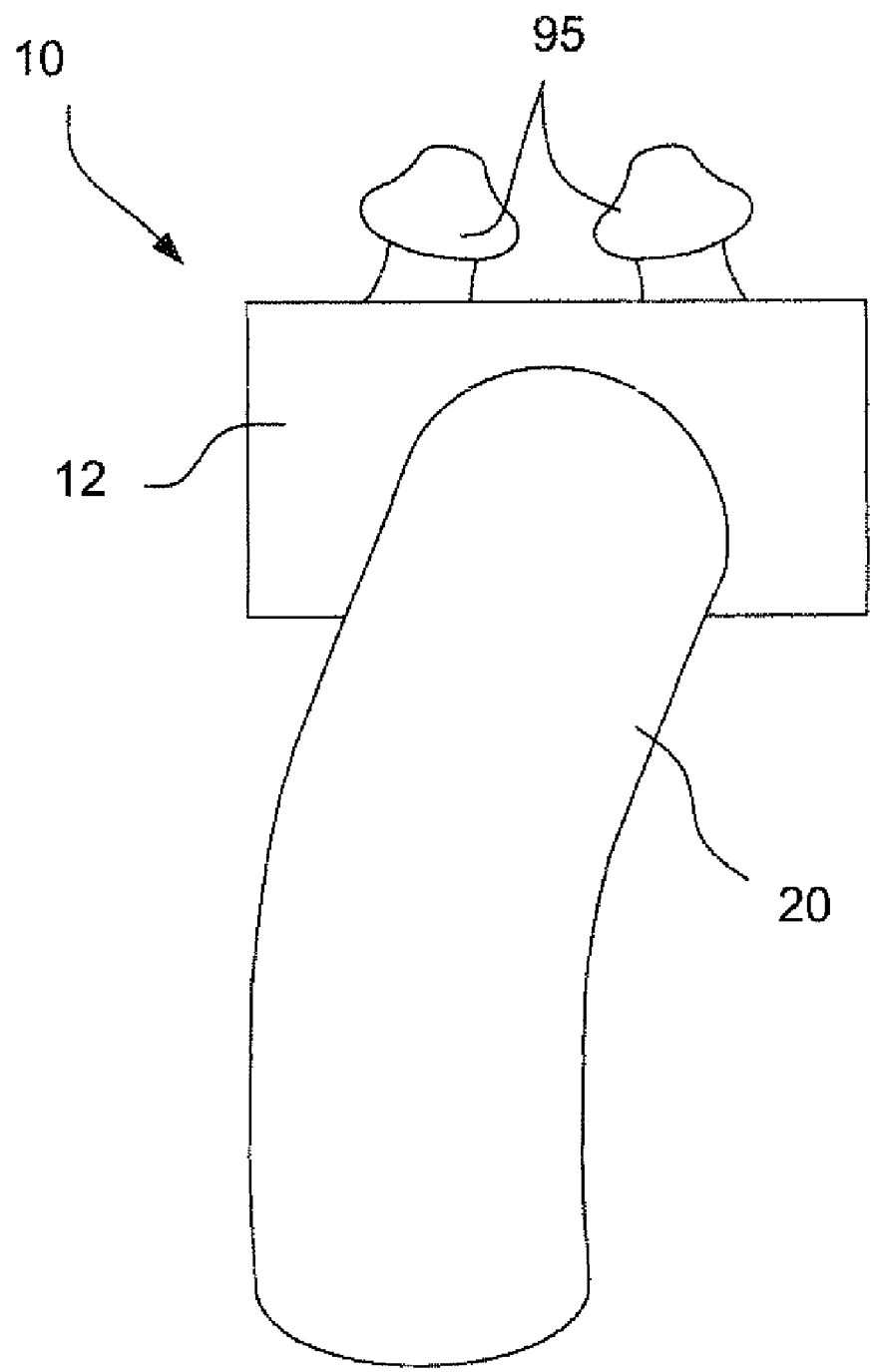
FIG. 10 is a schematic view of a respiratory mask including nasal prongs or nasal pillows according to an embodiment of the invention.

It should be appreciated that the gas washout vent may be provided to a nasal mask (e.g., FIG. 1) or full-face mask (e.g., FIG. 7) or nasal prongs or nasal pillows 95 (e.g., FIG. 10). The mask or nasal prongs or nasal pillows incorporates, or has in close proximity, the gas washout vent for venting exhaled gases to atmosphere. For example, the gas washout vent may be provided to the mask shell 12 or to the gas inlet 20.

Although the invention has been described with reference to specific examples, it is to be understood that these examples are merely illustrative of the application of the principles of the invention. Thus it is to be understood that numerous modifications may be made in the illustrative examples of the invention and other arrangements may be devised without departing from the spirit and scope of the invention.

We claim:

1. A respiratory mask comprising:
a patient interface structured for communication with a patient's airways in use;
a gas inlet to supply pressurized breathable gas in the range of 3-20 cm $H_2O$ to the patient interface; and
a gas washout vent portion having a plurality of holes therein, said holes having a diameter selected to allow adequate $CO_2$ washout from the patient interface at a lowest end of the pressure range,
wherein said plurality of holes is arranged in a plurality of rows, each said row having at least 3 of said holes, and
wherein each of the holes has a first end positioned on an inside surface of the mask and a second end positioned on an outer surface of the mask, and wherein the first end has a diameter that is smaller than a diameter of the second end.

2. A respiratory mask according to claim 1, wherein the patient interface comprises a cushion in the form of a nasal cushion, and the gas washout vent portion is provided on the gas inlet, said gas inlet being in the form of a rotatable elbow.

3. A respiratory mask according to claim 1, wherein the patient interface comprises a shell and a cushion in the form of nasal prongs or pillows provided on the shell, and the gas washout vent portion is provided to the shell and not the gas inlet.

4. A respiratory mask according to claim 1, wherein the patient interface includes a cushion in the form of a full face cushion and a shell on which the cushion is provided, and wherein the gas washout vent portion is provided to the shell.

5. A respiratory mask according to claim 1, wherein the plurality of holes includes at least 20 holes.

6. A respiratory mask according to claim 1, wherein the plurality of holes includes at least 30 holes.

7. A respiratory mask according to claim 1, wherein each of the holes is tapered in cross-section.

8. A respiratory mask comprising:
a patient interface;
a breathable gas inlet to provide pressurized gas at a pressure elevated above atmospheric pressure to the patient interface when the mask is in use; and
a gas washout vent including an air permeable portion to allow gas to exit from the patient interface, wherein the portion has at least ten through holes each having a length, a diameter, and a total open area due to the presence of the holes that are selected to help eliminate or reduce noise while maintaining sufficient $CO_2$ washout during patient breathing, and
wherein each of the holes has a first end positioned on an inside surface of the mask and a second end positioned on an outer surface of the mask, and wherein the first end has a diameter that is smaller than a diameter of the second end.

9. A respiratory mask according to claim 8, wherein the total open area is about 5% or more.

10. The respiratory mask according to claim 8, wherein the total open area is less than 25%.

11. A respiratory mask according to claim 8, wherein the patient interface comprises a nasal cushion or a full face cushion.

12. A respiratory mask according to claim 8, wherein the patient interface comprises nasal prongs or pillows.

13. A respiratory mask comprising:
a cushion;
a breathable gas inlet to provide pressurized gas at a pressure elevated above atmospheric pressure to the patient via the cushion when the mask is in use; and
at least one gas washout vent to allow gas to exit from the mask, wherein the washout vent has at least twenty through holes each having a length and a diameter that are selected to help eliminate or reduce noise while maintaining sufficient $CO_2$ washout during patient breathing, and
wherein each of the holes has a first end positioned on an inside surface of the mask and a second end positioned on an outer surface of the mask, and wherein the first end has a diameter that is larger than a diameter of the second end.

14. A respiratory mask according to claim 13, wherein each said hole has a length of about 0.5 mm.

15. A respiratory mask according to claim 13, wherein the cushion comprises a nasal cushion or a full face cushion.

16. A respiratory mask according to claim 13, wherein the cushion comprises nasal prongs or pillows.

17. A respiratory mask according to claim 13, wherein there are at least thirty through holes and the gas washout vent includes two vent portions.

18. A respiratory mask comprising:
a patient interface having a frame portion and a nose contacting portion in the form of nasal prongs or pillows, said frame portion and said nose contacting portion together defining a breathing cavity;
a breathable gas inlet to provide pressurized gas at a pressure elevated above atmospheric pressure to the patient interface when the mask is in use; and
a gas washout vent portion having at least twenty through holes to allow gas to quietly exit from the breathing cavity, wherein said holes are arranged in a plurality of rows,
wherein each of the holes has a first end positioned on an inside surface of the mask and a second end positioned on an outer surface of the mask, and wherein the first end has a different diameter than a diameter of the second end.

19. A respiratory mask according to claim 18, wherein the plurality of rows includes at least 4 rows each including at least 3 of said holes.

20. A respiratory mask according to claim 19, wherein the plurality of rows includes at least 5 rows each including at least 3 of said holes.

21. A respiratory mask according to claim 18, wherein the holes are provided on and extend through the gas inlet, and the holes are tapered such that an inner diameter of each hole oriented towards an inner surface of the gas inlet is smaller than an outer diameter on an outside surface of the gas inlet.

22. A CPAP apparatus comprising:
a blower to generate pressurized gas in the range of 3-20 cm $H_2O$; and
a mask according to claim 18.

23. A respiratory mask according to claim 18, further comprising a forehead support provided above the patient interface.

24. A respiratory mask according to claim 18, wherein the vent portion is provided on the frame portion.

25. A respiratory mask according to claim 18, wherein the vent portion is provided on the gas inlet.

26. A respiratory mask comprising:
a patient interface having a cushion;
a breathable gas inlet to provide pressurized gas at a pressure elevated above atmospheric pressure to a breathing cavity formed at least in part by the patient interface when the mask is in use; and a gas washout vent having a plurality of holes, said holes being structured and arranged to allow gas to be exhausted from the breathing cavity substantially without gas jetting, wherein:
the vent has a thickness of less than 3 mm, and
the vent includes at least 20 of said holes, said holes being arranged in a plurality of rows;
wherein each of the holes has a first end positioned on an inside surface of the mask and a second end positioned on an outer surface of the mask, and wherein the first end has a different diameter than a diameter of the second end.

27. A respiratory mask according to claim 26, wherein the plurality of rows includes at least 4 rows each including at least 3 of said holes.

28. A respiratory mask according to claim 27, wherein the plurality of rows includes at least 6 rows each including at least 3 of said holes.

29. A respiratory mask according to claim 28, wherein the plurality of rows includes at least 8 rows each including at least 3 of said holes.

30. A respiratory mask according to claim 18, wherein each of the holes has a first end positioned towards the breathing cavity and a second end positioned away from the breathing cavity, and wherein the first end has a diameter that is smaller than a diameter of the second end.

31. A respiratory mask according to claim 26, wherein the patient interface has a shell portion to support the cushion, and the cushion is in the form of nasal prongs or pillows, the holes being provided on the gas inlet.

32. A respiratory mask according to claim 26, wherein the patient interface includes a shell to support the cushion, and the cushion is in the form of a nasal cushion or a full face cushion, the holes being provided to the shell.

33. A respiratory mask according to claim 26, wherein each hole has a diameter of about 0.2 mm.

34. A respiratory mask according to claim 26, wherein the vent is formed on a membrane that is mounted to the patient interface.

35. A respiratory mask comprising:
a shell structured for communication with a patient's airways in use, the shell including a separately formed rotatable gas inlet to deliver pressurized breathable gas to the shell in the range of 3-20 cm $H_2O$;
a nasal-only cushion provided to the shell, the cushion and the shell defining a pressurized breathing cavity; and
a gas washout vent having a plurality of through holes, said through holes being configured and arranged to allow adequate $CO_2$ washout from the patient interface at a lowest end of the pressure range, said gas washout vent including an air permeable material interposed between an inner element having at least one opening and an outer element having at least one opening, such that $CO_2$ gas washout is directed from the breathing cavity and through the at least one opening of the inner element, the air permeable material and the at least one opening of the outer element.

36. A respiratory mask according to claim 35, wherein the inner element is formed as part of the shell.

37. A respiratory mask according to claim 35, wherein the inner and outer elements are mechanically interlocked with one another.

38. A respiratory mask according to claim 35, wherein the vent is provided to the gas inlet.

39. A respiratory mask comprising:
a patient interface structured for communication with a patient's airways in use;
a gas inlet in the form of a rotatable elbow to supply pressurized breathable gas in the range of 3-20 cm $H_2O$ to the patient interface; and
a gas washout vent having a plurality of holes, said holes being structured to allow adequate $CO_2$ washout from the patient interface at a lowest end of the pressure range, wherein said plurality of holes is arranged in a plurality of rows, each said row having at least 3 of said holes, and
wherein each of the holes has a first end positioned on an inside surface of the mask and a second end positioned on an outer surface of the mask, and wherein the first end has a diameter that is smaller than a diameter of the second end.

40. A respiratory mask according to claim 39, wherein each hole has a diameter of about 0.2 mm.

41. A respiratory mask according to claim 39, wherein the vent is formed on a membrane that is mounted on the patient interface.

42. A respiratory mask according to claim 39, wherein the patient interface comprises a cushion in the form of a nasal-only cushion or a full-face cushion, and the gas washout vent is provided on the rotatable elbow.

43. A respiratory mask according to claim 39, wherein the patient interface comprises a shell and a cushion in the form of nasal prongs or pillows provided to the shell, and the gas washout vent is provided to the rotatable elbow which is formed separately from the shell and rotatably mounted thereto.

44. A respiratory mask according to claim 39, wherein the patient interface includes a cushion in the form of a full face cushion and a shell on which the cushion is provided, and wherein the gas washout vent is provided to the shell.

45. A respiratory mask according to claim 39, wherein the plurality of holes includes at least 20 holes.

46. A respiratory mask according to claim 39, wherein the plurality of holes includes at least 30 holes.

47. A respiratory mask according to claim 39, wherein each of the holes is tapered in cross-section.

48. A respiratory mask comprising:
a patient interface;
a breathable gas inlet to provide pressurized gas at a pressure elevated above atmospheric pressure to the patient interface when the mask is in use; and
a gas washout vent to allow gas to exit from the patient interface, wherein the vent has at least ten through holes to maintain sufficient $CO_2$ washout during patient breathing while avoiding or reducing exhaust gas jetting and/or noise as perceived by the patient; and
wherein each of the holes has a first end positioned on an inside surface of the mask and a second end positioned on an outer surface of the mask, and wherein the first end has a diameter that is smaller than a diameter of the second end.

49. A respiratory mask according to claim 48, wherein the patient interface comprises a nasal-only cushion or a full face cushion.

50. A respiratory mask according to claim 48, wherein the patient interface comprises nasal prongs or pillows.

51. A respiratory mask comprising:
   a cushion;
   a breathable gas inlet to provide pressurized gas at a pressure elevated above atmospheric pressure to the patient via the cushion when the mask is in use; and
   at least one gas washout vent to allow gas to exit from the mask, wherein the washout vent has an array of at least 20 through holes grouped to avoid or reduce air jetting;
   wherein each of the holes has a first end positioned on an inside surface of the mask and a second end positioned on an outer surface of the mask, and wherein the first end has a different diameter than a diameter of the second end.

52. A respiratory mask according to claim 51, wherein each of the holes has a first end positioned on an inside surface of the mask and a second end positioned on an outer surface of the mask, and wherein the first end has a diameter that is larger than a diameter of the second end.

53. A respiratory mask according to claim 51, wherein each said hole has a length of about 0.5 mm and a diameter of about 0.2 mm.

54. A respiratory mask according to claim 51, wherein the cushion comprises a nasal-only cushion or a full face cushion and the washout vent includes at least 40 through holes.

55. A respiratory mask according to claim 51, wherein the cushion comprises nasal prongs or pillows and the washout vent includes at least 40 through holes.

56. A respiratory mask comprising:
   a patient interface structured for communication with a patient's airways in use, the patient interface including a swivel elbow;
   said patient interface including a cushion, the cushion at least partly defining a pressurized breathing cavity pressurized to a pressure in the range of 3-20 cm $H_2O$ in use;
   said patient interface including a gas washout vent having an array of through holes extending from an inside of the elbow to an outside of the elbow, said array of through holes, in use, allowing $CO_2$ washout from the breathing cavity to atmosphere at a lowest end of the pressure range while reducing or avoiding air jetting and/or noise perceived by the patient,
   each of said holes having a generally tapered shape such that an inside diameter of each hole that is positioned on the inside of the elbow is smaller than an outside diameter of the corresponding hole that is positioned on the outside of the elbow.

57. A respiratory mask according to claim 56, wherein the array of through holes includes at least 4 rows of said through holes, and said row including at least 3 of said holes.

58. A respiratory mask according to claim 57, wherein each of the rows has at least 5 of said holes.

59. A respiratory mask according to claim 57, wherein the plurality of rows includes at least 6 rows each including at least 3 of said holes.

60. A respiratory mask according to claim 59, wherein the plurality of rows includes at least 8 rows each including at least 5 of said holes.

61. A respiratory mask according to claim 56, wherein each hole has a diameter of about 0.2 mm.

62. A respiratory mask according to claim 56, wherein the plurality of holes is formed on a membrane attached to the elbow.

63. A respiratory mask according to claim 61, wherein the elbow has a first portion coupled to the shell and a second portion, formed at an angle of about 90° relative to the first portion.

64. A respiratory mask according to claim 63, wherein the vent is positioned on the first portion of the elbow.

65. A respiratory mask according to claim 63, wherein the vent is positioned on the second portion of the elbow.

66. A respiratory mask according to claim 56, wherein the cushion comprises nasal prongs or nasal pillows.

67. A respiratory mask according to claim 56, wherein the cushion comprises a nasal-only cushion.

68. A respiratory mask comprising:
   a shell structured for communication with a patient's airways in use, the shell defining a nasal bridge region formed at or near an apex of the shell;
   a swivel elbow mounted to the shell;
   a cushion provided to the shell, the cushion and the shell defining a breathing cavity to receive gas pressurized in the range of 3-20 cm $H_2O$; and
   a gas washout vent provided to the shell, said gas washout vent being positioned above the elbow and between the elbow and the nasal bridge region of the shell, said washout vent having a plurality of through holes extending from an inside of the shell to an outside of the shell, said through holes, in use, allowing $CO_2$ washout from the breathing cavity to atmosphere at a lowest end of the pressure range,
   wherein each of the holes has a first end positioned on the inside of the shell and a second end positioned on the outside of the shell, and wherein the first end has a different diameter than a diameter of the second end,
   wherein each of said holes has a generally tapered shape such that an inside diameter of each hole that is positioned on the inside of the shell is smaller than an outside diameter of the corresponding hole that is positioned on the outside of the shell.

69. A respiratory mask according to claim 68, further comprising an arm formed on the shell, said arm being structured to extend generally between the eyes in use, said arm having a distal end portion with a fitting, said fitting having a center portion supporting a forehead pad and a lateral upper slot provided on each side of the center portion to receive an end of an upper mask retaining strap.

70. A respiratory mask according to claim 69, wherein said vent is provided between the elbow and the arm.

71. A respiratory mask according to claim 69, further comprising a pair of lower slots positioned generally adjacent the elbow, each of the lower slots coupled with a lower mask retaining strap.

72. A respiratory mask according to claim 68, wherein the plurality of through holes are arranged in an array which is grouped to allow the exhaust of $CO_2$ gas washout while reducing or avoiding noise and/or gas jetting as perceived by the patient.

73. A respiratory mask according to claim 72, wherein the plurality of through holes includes at least 20 through holes.

74. A respiratory mask according to claim 73, wherein the plurality of through holes includes at least 30 through holes.

75. A respiratory mask according to claim 74, wherein the plurality of through holes includes at least 40 through holes.

76. A respiratory mask according to claim 72, wherein the plurality of through holes in said array are arranged in a plurality of rows each having at least 5 through holes.

77. A respiratory mask according to claim 76, wherein the plurality of rows includes at least 4 rows.

78. A respiratory mask according to claim 76, wherein the plurality of rows includes at least 6 rows.

79. A respiratory mask according to claim 76, wherein the plurality of rows includes at least 8 rows.

80. A respiratory mask according to claim 68, wherein the cushion comprises a full-face cushion.

81. A respiratory mask according to claim 68, wherein the plurality of through holes includes at least 20 through holes.

82. A respiratory mask according to claim 68, wherein the plurality of through holes in said array are arranged in a plurality of rows each having at least 5 through holes.

83. A nasal respiratory mask, comprising:
- a shell structured for communication with a patient's airways in use, the shell including a separately formed rotatable gas inlet to deliver pressurized breathable gas to the shell in the range of 3-20 cm $H_2O$;
- a nasal-only cushion provided to the shell, the cushion and the shell defining a pressurized breathing cavity;
- a fixed forehead support including an arm extending from the shell and a fitting provided to a distal end of the arm, the fitting having a center portion supporting a forehead pad and a lateral upper slot provided on each side of the center portion adapted to be coupled with an upper mask retaining strap;
- the shell including a pair of lateral lower slots on respective sides of the shell, each of the lower slots adapted to be coupled with a lower mask retaining strap;
- an insert having a plurality of gas washout through holes provided in an opening on the shell,
- wherein each of the holes has a first end oriented towards an inside surface of the mask and a second end oriented towards an outer surface of the mask, and wherein the first end has a diameter that is larger than a diameter of the second end,
- wherein the plurality of through holes are arranged in a plurality of rows, each said row having at least 3 of said holes.

84. A nasal respiratory mask according to claim 83, wherein the plurality of rows includes at least 6 rows.

85. A nasal respiratory mask according to claim 83, wherein the plurality of through holes includes at least 40 holes.

86. A nasal respiratory mask according to claim 83, wherein the through holes are provided on and extend through the gas inlet.

87. A nasal respiratory mask according to claim 86, wherein the gas inlet is in the form of an elbow having a first portion coupled to the shell and a second portion formed at an angle of about 90° relative to the first portion.

88. A nasal respiratory mask according to claim 87, wherein the vent is positioned on the first portion of the elbow.

89. A nasal respiratory mask according to claim 83, wherein the opening to which the insert is attached is positioned on the gas inlet.

90. A nasal respiratory mask according to claim 83, wherein the insert is located against an outer surface of the shell by a flange.

91. A respiratory mask according to claim 26, wherein the pressurized gas is in the range of 3-20 cm $H_2O$.

92. A respiratory mask according to claim 51, wherein the pressurized gas is in the range of 3-20 cm $H_2O$.

* * * * *